US006416478B1

(12) United States Patent
Hossack

(10) Patent No.: US 6,416,478 B1
(45) Date of Patent: Jul. 9, 2002

(54) EXTENDED BANDWIDTH ULTRASONIC TRANSDUCER AND METHOD

(75) Inventor: John A. Hossack, Palo Alto, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/466,679

(22) Filed: Dec. 20, 1999

Related U.S. Application Data

(63) Continuation-in-part of application No. 09/406,511, filed on Sep. 28, 1999, now abandoned, which is a continuation of application No. 09/129,181, filed on May 5, 1998, now Pat. No. 5,957,851.

(51) Int. Cl.[7] ................................................. A61B 8/00

(52) U.S. Cl. ...................................................... 600/459

(58) Field of Search .......................... 600/447, 443, 600/449, 455, 459, 460, 461, 454

(56) References Cited

U.S. PATENT DOCUMENTS

| 4,096,756 A | 6/1978 | Alphonse |
| 4,240,003 A | 12/1980 | Larson, III |
| 4,276,491 A | 6/1981 | Daniel |
| 4,354,132 A | 10/1982 | Borbough et al. |
| 4,356,422 A | 10/1982 | Van Maanen |
| 4,427,912 A | 1/1984 | Bui et al. |
| 4,446,739 A | 5/1984 | Coursant |
| 4,550,607 A | 11/1985 | Maslak et al. |
| 4,712,037 A | 12/1987 | Verbeek et al. |
| 4,735,096 A | 4/1988 | Dorr |
| 4,736,631 A | 4/1988 | Takeuchi et al. |
| 5,115,809 A | 5/1992 | Saitoh et al. |
| 5,158,071 A | 10/1992 | Umemura et al. |
| 5,163,436 A | 11/1992 | Saitoh et al. |
| 5,305,756 A | 4/1994 | Entrekin et al. |
| 5,345,139 A | 9/1994 | Gururaja et al. |
| 5,381,067 A | 1/1995 | Greenstein et al. |
| 5,389,848 A | 2/1995 | Trzaskos |
| 5,396,143 A | 3/1995 | Seyed-Bolorforosh et al. |
| 5,410,205 A | 4/1995 | Gururaja |
| 5,410,516 A | 4/1995 | Uhlendorf et al. |
| 5,415,175 A | 5/1995 | Hanafy et al. |
| 5,423,220 A | 6/1995 | Finsterwald et al. |
| 5,435,311 A | 7/1995 | Umemura et al. |
| 5,438,554 A | 8/1995 | Seyed-Bolorforosh et al. |
| 5,438,998 A | 8/1995 | Hanafy |
| 5,446,333 A | 8/1995 | Ishida et al. |
| 5,724,976 A | * 3/1998 | Mine et al. .................. 600/443 |
| 5,825,117 A | 10/1998 | Ossmann et al. |
| 5,957,851 A | 9/1999 | Hossack |

FOREIGN PATENT DOCUMENTS

WO    WO 94/16826    8/1994

OTHER PUBLICATIONS

Sittig, E., "Transmission Parameters of Thickness–Drive Piezoelectric Transducers Arranged in Multilayer Configurations," IEEE Transactions on sonics and Ultrasonics, vol. SU–14, No. 4, Oct. 1967, pp. 167–174.

(List continued on next page.)

Primary Examiner—Marvin M. Lateef
Assistant Examiner—Maulin Patel
(74) Attorney, Agent, or Firm—Craig A. Summerfield; Brinks Hofer Gilson & Lione

(57) ABSTRACT

An ultrasound transducer that allows transmission of pressure waves at a first frequency and reception of pressure waves at a second frequency. Each transducer element is formed by multiple layers of transducer material. A transceiver provides an excitation signal to the transducer and receives energy from the transducer. All of the layers are coupled to the transceiver during transmission so that all of the layers are activated. Some of the layers are decoupled from the transceiver during reception so that not all of the layers contribute to the received signal. A filter circuit is also responsive to the coupling, providing additional low, high or band pass filtering appropriate for one of transmit or receive. The pressure waves at the second frequency are responsive to tissue and/or contrast agents.

42 Claims, 10 Drawing Sheets

OTHER PUBLICATIONS

Burckhardt, C.B., "Ultrasound Axicon: a device for focusing over a large depth," E. Hoffman–LaRoche & Company, vol. 54, No. 6, 1973, pp. 1628–1630.

Yamada, K. et al., "Conical and Toroidal Piezoelectric Polymer Transducers for Long Range Focusing," Ultrasonic Symposium, 1982, pp. 837–840.

"Apodized Conical Focusing for Ultrasound Imaging," IEEE Transactions on Sonics & Ultrasonics, vol. SU–29, No. 3, May 1982, pp. 128–138.

Patterson, M. et al., "Acoustic Fields of Conical Radiators," Ultrasonic B–Scan Images, IEEE Transactions on Sonics and Ultrasonics, vol. SU–29, No. 2, Mar. 1982, pp. 83–92.

Xu, Q. C. et al. "Composite Transducer with Multiple Piezoelectric Matching Layers," Ultrasonics Symposium, 1988, pp 507–512.

Bao, X. Q. et al., "Model of a Bilaminar Actuator for Active Acoustic Control Systems," J. Acoust. Soc. Am 87(3), Mar. 1990, pp. 1350–1352.

Translation of European Patent No. 0 357 164, by J. Atkinson, 1991.

Chofflet, L. et al., "A Multi–Piezoelectric Structure: The Stacked Transducer," Ultrasonics Symposium, 1991, pp. 611–614.

Hossack, J.A., et al. "Multi Layer Transducers for Broadband Applications," Ultrasonics Symposium, 1991, pp. 605–610.

Schrope, B. et al., "Simulated Capillary Blood Flow Measurement Using a Nonlinear Ultrasonic Contrast Agents," Ultrasonic Imaging 14, 1992, pp. 134–158.

Hossack, J.A. et al., "Improving Transducer Performance Using Multiple Active Layers," SPIE vol. 1733, 1992, pp. 284–296.

Hossack, J.A., et al., "Improving the Characteristics of a Transducer Using Multiple Piezoelectric Layers," IDDD Transactions on Ultrasonics, Ferroelectrics, and Frequency Control, vol. 40, No. 2, Mar., 1993, pp. 131–139.

Russell, L.B., et al., Thickness–Mode Modeling of Active Multi–Layered Piezoelectric Transducers and the Application to "SMART" Sensor Design, Ultrasonics Symposium, 1994, pp. 615–618.

Strout, T., et al., "Relaxor Ferroelectric Materials," Ultrasonics Symposium, 1990, pp. 711–720.

Takeuchi, H. et al., "Medical Ultrasonic Probe Using Electrostrictive–Ceramics/Polymer Composite" Ultrasonics Symposium, 1989, pp. 705–708.

D. Damjanovic, et al., "Electrostrictive and Piezoelectric Materials for Actuator Applications," J. of Inell, Mater. Syst. And Struct. vol. 3, Apr. 1992, pp. 190–208.

Volkmar Uhlendorf et al. Nonlinear Acoustical Response of Coated Microbubbles in Diagnostic Ultrasound, 1994; pp. 1559–1562.

Charles S. DeSilets; "Thesis by DeSilets"; Stanford University; 1978; pp. 1–172.

Alan Robert Selfridge; "The Design and Fabrication of Ultrasonic Transducers and Tranducer Array"; Jul. 1982— Stanford University; pp. 1–183.

* cited by examiner

TRANSDUCER RESPONSE (—) AND DESIRED TRANSMIT AND RECEIVE RESPONSES (-)

DESIRED (-) AND OBTAINED RESULTS (—)

EXTENDED BANDWIDTH ULTRASONIC TRANSDUCER AND METHOD

RELATED APPLICATIONS

This application is a continuation-in-part of U.S. Application Ser. No. 09/406,511 (now abandoned), filed Sep. 28, 1999 which is a continuation of 09/129,181 filed May 5, 1998 now U.S. Pat. No. 5,57,851, the disclosures of which are incorporated herein by reference.

FIELD OF THE INVENTION

This invention relates to transducers and more particularly to phased array transducers for use particularly in the medical diagnostic field.

Ultrasound machines are often used for observing organs in the human body. Typically, these machines contain transducer arrays for converting electrical signals into pressure waves and vice versa. Generally, the transducer array is in the form of a hand-held probe which may be adjusted in position to direct the ultrasound beam to the region of interest.

FIG. 1 illustrates a prior art transducer array 10 for generating an ultrasound beam. Typically, such an array may have 128 transducer elements 12 in the azimuthal direction. Adapted from radar terminology, the x, y, and z directions are referred to as the azimuthal, elevation, and range directions, respectively.

Each transducer element 12, typically rectangular in cross-section, includes a first electrode 14, a second electrode 16 and a piezoelectric layer 18. In addition, one or more acoustic matching layers 20 may be disposed over the piezoelectric layer 18 to increase the efficiency of the sound energy transfer to the external medium. The electrode 14 for a given transducer element 12 may be part of a flexible circuit 15 for providing the hot wire or excitation signal to the piezoelectric layer 18. Electrode 16 for a given transducer element may be connected to a ground shield return 17. The piezoelectric layer 18 is metalized on its top and bottom surfaces and the matching layer 20 is also metalized on all surfaces so that electrode 16 which is in physical contact with the matching layer 20 is electrically coupled to a surface of the piezoelectric layer 18 by the metallization.

The transducer elements 12 are disposed on a backing block 24. The backing block 24 may be highly attenuative such that ultrasound energy radiated in its direction (i.e., away from an object 32 of interest) is substantially absorbed. In addition, a mechanical lens 26 may be placed on the matching layer 20 to help confine the generated beam in the elevation-range plane and focus the ultrasound energy to a clinically useful depth in the body. The transducer array 10 may be placed in a nose piece 34 which houses the array. Examples of prior art transducer structures are disclosed in Charles S. DeSilets, *Transducer Arrays Suitable for Acoustic Imaging*, Ph.D. Thesis, Stanford University (1978) and Alan R. Selfridge, *Design and Fabrication of Ultrasonic Transducers and Transducer Arrays*, Ph.D. Thesis, Stanford University (1982).

Individual elements 12 are electrically excited by electrodes 14 and 16 with different amplitude and phase characteristics to steer and focus the ultrasound beam in the azimuthal-range plane. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen. When an electrical signal is imposed across the piezoelectric layer 18, the thickness of the layer changes slightly. This property is used to generate sound from electrical energy. Conversely, electrical signals are generated across the electrodes in contact with the piezoelectric layer 18 in response to thickness changes that have been imposed mechanically from sound waves reflected back to the piezoelectric layer 18.

The pressure waves generated by the transducer elements 12 are directed toward an object 32 to be observed, such as the heart of a patient being examined. Each time the pressure wave confronts tissue having different acoustic characteristics, a wave is reflected backward. The array of transducers may then convert the reflected pressure waves into corresponding electrical signals.

For the transducer shown in FIG. 1 the beam is said to be mechanically focused in the elevation direction. The focusing of the beam in the azimuthal direction is done electronically by controlling the timing of the transmissions of each transducer element. This may be accomplished by introducing appropriate phase delays in the firing signals.

Reflected energy from a particular location in the imaging plane is collected by the transducer elements. The resultant electronic signals from individual transducer elements are individually detected and reinforced by introducing appropriate delays. Extensive processing of such data from the entire imaging phase is done to generate an image of the object. Such an image is typically displayed on a CRT monitor.

Sometimes it is desirable to image particular features to the exclusion of others. For example, it may be desirable to image the flow of blood in a patient to the exclusion of the surrounding organs and muscles. Introducing contrast agents into the patient's bloodstream allows the imaging of the blood stream. Contrast agents may be in the form of a solution or suspension of microbubbles or agents that produce microbubbles. The use of contrast agents provides selective evaluation of the signal components affected by the materials or media which have been introduced. This has the advantage that selective representation of the region filled with those agents is possible without finding the difference between two or more conditions recorded before and after application of the materials or media.

Nonlinear contrast agents are described for example by V. Uhlendorf, et al., in "Nonlinear Acoustical Response of Coated Microbubbles in Diagnostic Ultrasound" (1995) Ultrasonic Symposium, pp. 1559–1562). Such agents possess a fundamental resonant frequency. When they are insonified with high intensity ultrasonic energy at this fundamental frequency, they radiate ultrasonic frequency at a harmonic of the fundamental frequency. Such contrast agents are often used to highlight regions containing blood loaded with the contrast agent. For example, in the case of a blood-filled chamber of the heart, the borders of the chamber can be distinguished more easily when contrast agent is used. Since the contrast agent generates harmonic ultrasound energy, echoes from tissue (containing no contrast agent) at the fundamental frequency may be eliminated or reduced by filtering at the receive beamformer. Because most transducers operate in the half wavelength resonance mode they are not able to effectively receive energy at a second harmonic frequency since at the second harmonic frequency, the transducer elements are approximately one wavelength thick. This causes the charge generated on the two halves of the transducer element to be out of phase with each other which results in a cancellation or a null.

A wideband transducer can be operated to transmit pressure waves at one frequency and receive second harmonic frequency signals reflected back. FIG. 2 is a graph illustrating the transmit response from a transducer having a wide bandwidth, for example 70%. A bandwidth of 70% means that the bandwidth measured between the lower frequency at which the sensitivity is −6dB with respect to the maximum sensitivity attained over the useful frequency range of the transducer and the upper frequency at which the sensitivity is −6dB with respect to the maximum sensitivity is 70% of the center frequency where the center frequency is defined as the average of the lower and upper −6dB frequencies. Using a transducer with a center frequency $f_c$ of 4.5 MHz, an ultrasound wave can be transmitted at 2/3 $f_c$ or 3 MHz and received at 4/3 $f_c$ or 6 MHz.

While energy may be transmitted and received within the transducer's available bandwidth, there are several disadvantages associated with using a wideband transducer in such a manner. Because transducer bandwidths are typically 75% and less, it is necessary to work near the edges of the transducer's bandwidth in order to transmit at one frequency and receive at another. This results in lower sensitivity and undesirable filtering effects on the lower edge of the spectrum in transmit and on the upper end of the spectrum on receive as will be illustrated in the graphs of FIGS. 3 and 4. Ideally it is desirable to operate near the center of the available bandwidth for maximum sensitivity and spectral purity.

FIG. 3 is a graph illustrating the transducer transmit response (in dashed line) and the desired transmit response and receive response centered at 2/3 $f_c$ and 4/3 $f_c$ respectively (in solid line). FIG. 4 is a graph illustrating the filtering effect of operating a wide bandwidth transducer near the edges of its bandwidth. The desired transmit and receive response are shown in solid line and the distorted, filtered transmit and receive response are shown in dashed line. It can be seen that a portion of the desired spectra has been removed by the filtering effect of the transducer.

It is thus desirable to provide a transducer structure that can be optimized to transmit pressure waves at one frequency and receive energy at another frequency. More particularly, it is desirable to provide a transducer that can generate pressure waves at a first fundamental frequency and receive pressure waves at a second harmonic frequency.

SUMMARY

According to a first aspect there is provided an ultrasound transducer probe for transmitting an ultrasound beam into an area of examination and receiving signals reflected from said area of examination. The ultrasound transducer probe includes a first layer having a first electrode on one side of the first layer and a second electrode on an opposite side of the first layer. The first layer emits an ultrasound beam when a signal is applied to the first and second electrodes and the first layer develops a signal across the first and second electrodes upon receipt of an ultrasound beam reflected back from the area of examination. A second layer is disposed on the first layer. The second layer has a third electrode on one side of the second layer and a fourth electrode on an opposite side of the second layer. The second layer emits an ultrasound beam when a signal is applied to the third and fourth electrodes and the second layer develops a signal across the third and fourth electrodes upon receipt of an ultrasound beam reflected back from the area of examination. Means for isolating the signal developed across the second layer are provided as well as at least one tuning element.

According to a second aspect, there is provided a method for imaging an area of examination by transmitting an ultrasound beam into the area of examination and receiving signals reflected back from the area of examination. The method includes the steps of providing an ultrasound transducer having at least a first layer and a second layer, disposed on the first layer, transmitting an ultrasound beam by applying a signal across both the first and second layers, receiving signals generated across the first layer while isolating signals generated across the second layer, and filtering one of the transmit and receive signals as a function of the isolation.

According to a third aspect, there is provided a method for imaging an area of examination by transmitting an ultrasound beam into the area of examination and receiving signals reflected back from the area of examination. The area of examination is substantially free of contrast agents during an entire imaging session. The method includes the steps of providing an ultrasound transducer having at least a first layer and a second layer, disposed on the first layer, transmitting an ultrasound beam by applying a signal across both the first and second layers, and receiving signals generated across the first layer while isolating signals generated across the second layer.

The invention itself, together with further objects and attendant advantages, is defined by the following claims and will best be understood by reference to the following detailed description, taken in conjunction with the accompanying drawings.

DETAILED DESCRIPTION OF THE PRESENTLY PREFERRED EMBODIMENTS

Figure 1:
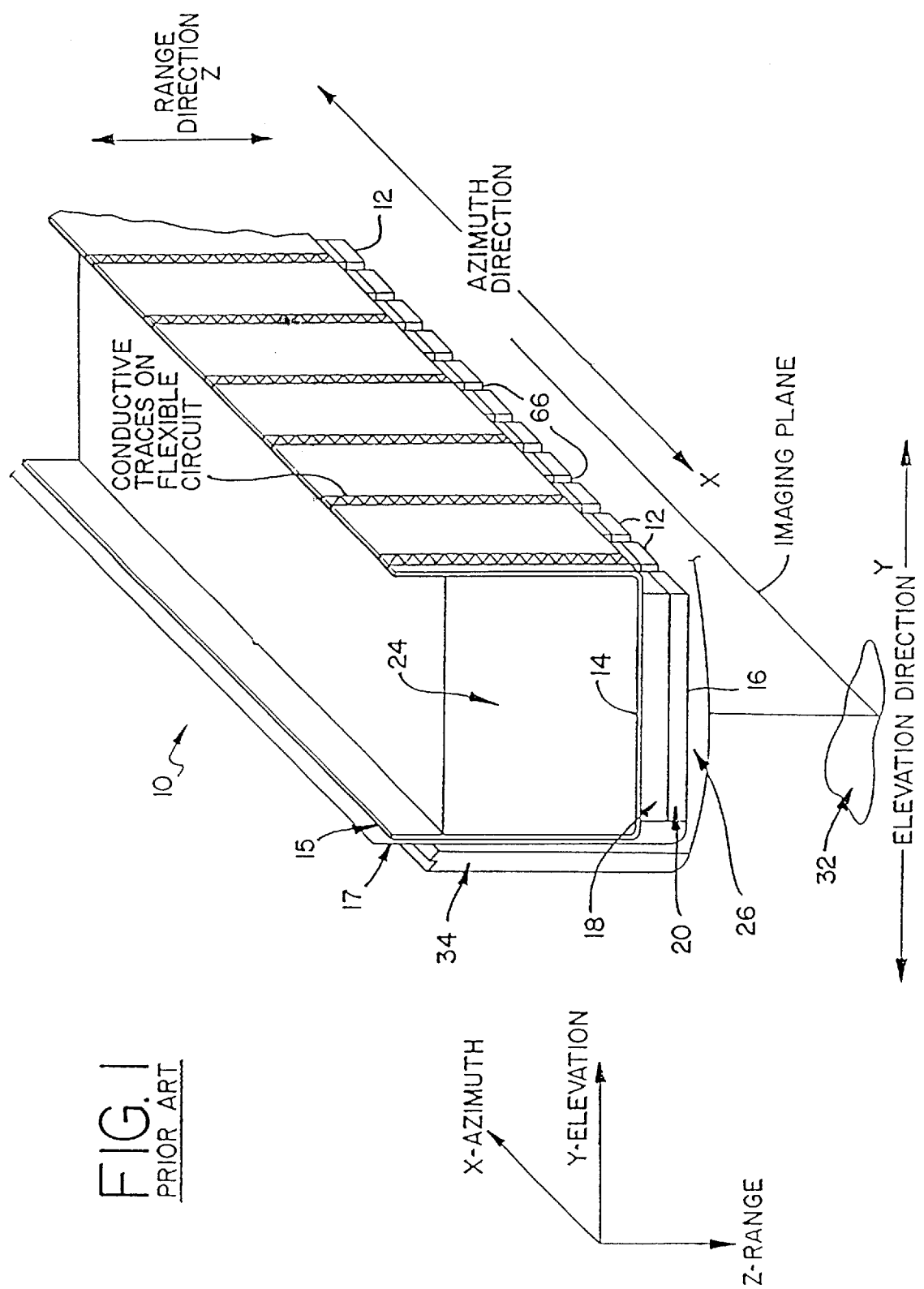
FIG. 1 illustrates a prior art transducer array for generating an ultrasound beam.
Figure 2:
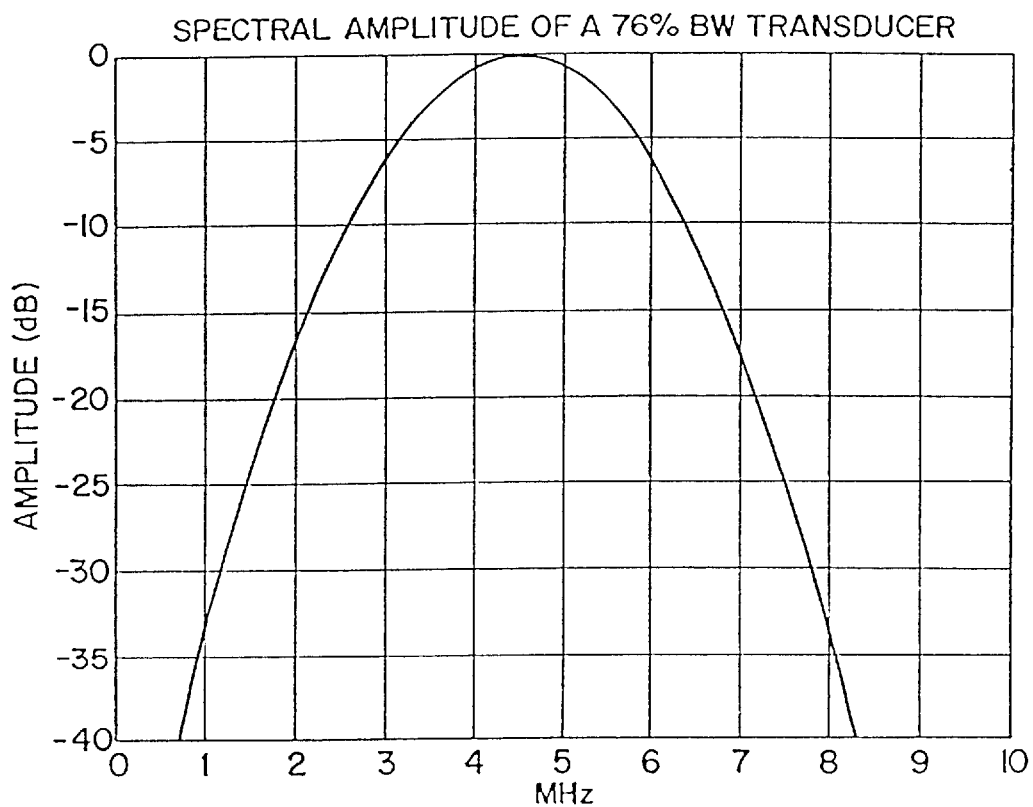
FIG. 2 is a graph illustrating the transmit response from a transducer having a wide bandwidth.
Figure 5:
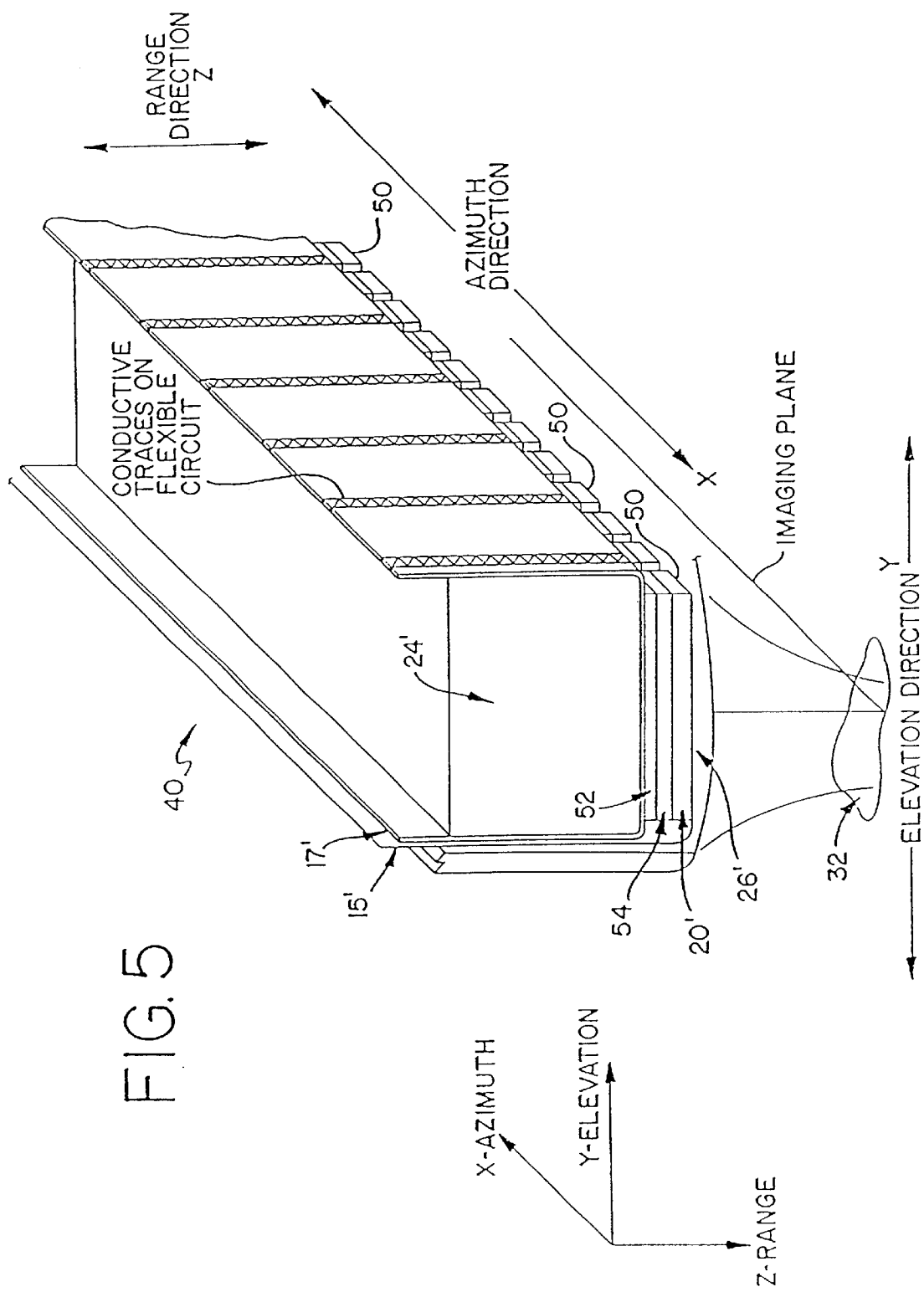
FIG. 5 is a schematic view of a transducer array according to a first preferred embodiment of the present invention.

FIG. 5 is a schematic of a transducer array 40 according to a first preferred embodiment of the present invention. The transducer array 40 has many of the same components as the transducer array 10 shown in FIG. 1. Therefore, like reference numerals, primed, will be used to identify like components. The transducer array 40 includes a backing block 24', an interconnecting or flexible circuits 15' and 17' and a plurality of transducer elements 50. In a preferred embodiment, the transducer array 40 includes one or more acoustic matching layers 20' disposed over the transducer elements 50. In addition, a lens 26' may be placed on the acoustic matching layer 20'. The plurality of transducer elements 50 are arranged along the azimuthal direction.

Each transducer element 50 is formed by multiple layers of transducer material. In a preferred embodiment a double layer transducer is shown having a first layer 52 and a second layer 54 disposed on the first layer 52. Of course, more than two layers may be provided. In addition, an intermediate layer may be disposed between the first and second layers. Multi-layer transducers are typically employed where it is necessary to stack transducer layers in order to improve electrical matching to cable and system. Such stacked layers are acoustically in series and electrically in parallel. The flexible circuits 15' and 17' are coupled to the electrodes on the first and second layers 52 and 54 of the transducer as will be discussed in detail hereinafter. A third flexible circuit (not shown) is coupled to the abutting electrodes of the first and second layer.

In a preferred embodiment, the first and second layers 52 and 54 are composed of lead zirconate titanate (PZT) such as 3203HD commercially available from Motorola Ceramic Products of Albuquerque, N. Mex. Alternatively, the first and second layers 52 and 54 may be formed from a composite material of piezoelectric ceramic posts embedded in polymer or PVDF piezoelectric polymer material. In addition, both layers do not have to be made of the same material. One could be formed from PZT while the other is a PZT composite or PVDF layer, for example. The first layer 52 and the second layer 54 each preferably have a thickness of about 0.009 inches. Alternatively, the thickness of each layer may range from about 0.006 to about 0.012 inches. In addition, both layers need not have the same thickness.

In a preferred embodiment the backing block 24' is formed of a filled epoxy comprising Dow Corning's part number DER 332 treated with Dow Corning's curing agent DEH 24 and has an aluminum oxide filler. Preferably the acoustic matching layer 20 or layers may have a high impedance or a low impedance or both when multiple matching layers are used. A low impedance matching layer may be formed of Dow Corning's epoxy DER 332 plus Dow Corning's curing agent DEH 24. For a high impedance acoustic matching layer the same materials may be used plus a filler of 1 micron tungsten carbide and 9 micron alumina particles which are added to obtain an acoustic impedance of approximately 10.0 MRayls.

Figure 6:
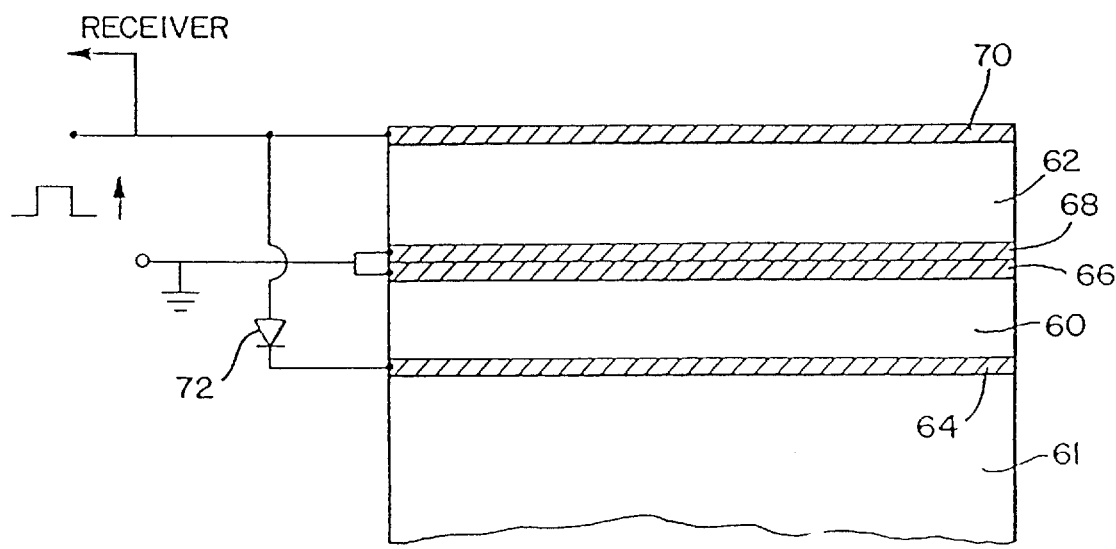
FIG. 6 illustrates a cross-sectional view taken along the elevation direction of a transducer array according to a preferred embodiment of the present invention.
Figure 3:
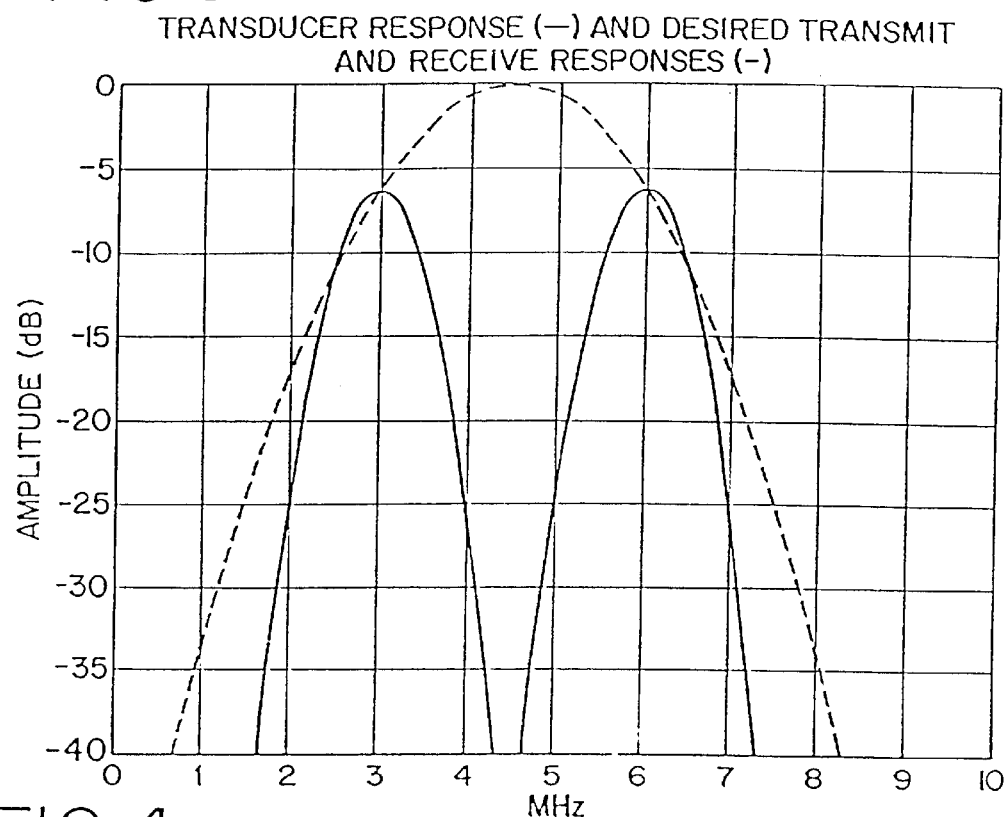
FIG. 3 is a graph illustrating the transducer transmit response and the desired transmit response and receive response.
Figure 4:
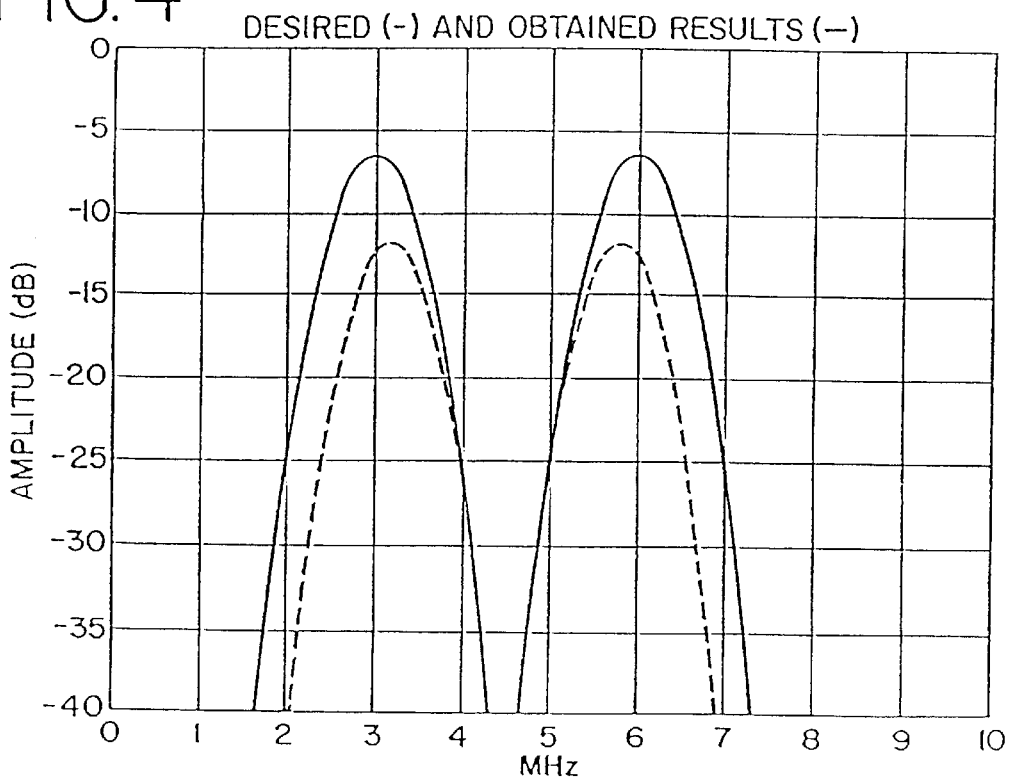
FIG. 4 is a graph illustrating the filtering effect of operating a wide bandwidth transducer near the edges of its bandwidth.

FIG. 6 illustrates a cross-sectional view taken along the elevation direction of a transducer array according to a preferred embodiment of the present invention. The transducer array preferably includes a first layer 60 of piezoelectric material and a second layer 62 of piezoelectric material disposed on the first layer 60. Both layers are disposed on a backing block 61. The first layer 60 has a first electrode 64 on one surface and a second electrode 66 on an opposite surface. The second layer 62 also has a first electrode 68 on one surface and a second electrode 70 on an opposite surface. Alternatively, electrodes 66 and 68 may be formed as one electrode between the first and second layer. Standard electrodes are available from the PZT manufacturer. Preferably the electrodes are formed of gold sputtered over a nickel chrome adhesion layer.

The second electrode 66 of the first layer 60 and the first electrode 68 of the second layer 62 abut one another and are coupled to ground as shown. The second electrode 70 of the second layer 62 is preferably permanently coupled to a transceiver (not shown) of the transducer system. The first electrode 64 of the first layer 60 is coupled to the transceiver through a diode 72.

The first electrode 64 of the first layer 60 and the second electrode 70 of the second layer 62 may be part of a flexible circuit such as 15' and 17' as shown in FIG. 5 for providing the hot wire or excitation signal to the first and second layers 60 and 62, respectively. A flexible circuit may be any interconnecting design used in the acoustic or integrated circuit fields, for example. The flexible circuit is typically made of a copper layer carrying a lead for exciting the transducer element. The copper layer may be bonded to a piece of polyimide material, typically KAPTON. In the region of the transducer element both sides of the copper flexible circuit should be exposed, i.e. free from polyimide so that electrical contact to the top and bottom electrodes of the piezoelectric layers is facilitated. Preferably the copper layer is coextensive in size with the transducer element. In addition, the interconnect circuit may be gold plated to improve the contact performance. Such a flexible circuit is manufactured by Sheldahl of Northfield, Minn. The ground electrode may also be formed by a flexible circuit.

The transceiver transmits an excitation signal to the transducer array and receives signals from the transducer array. In this particular embodiment the transceiver emits an excitation signal in the form of a positive pulse as shown. The voltage of the excitation signal is generally significantly greater than the diode turn-on voltage and thus during transmit, both the first and second layers 60 and 62 are activated. The excitation signal may be modified to accommodate the presence of diode 72 so that the voltage across the first layer 60 is as required, i.e., if the diode has a voltage drop of 0.7 volts, the amplitude of the excitation signal may be increased by 0.7 volts.

In the reception mode, the voltage generated across the first layer 60 and the second layer 62 from a pressure wave reflected back by the object being examined is on the order of a few millivolts. The voltage across the first layer 60 does not exceed the turn-on voltage of the diode 72. Therefore diode 72 isolates the first layer 60 from the transceiver during reception. Alternatively, the second layer 62 may be isolated by coupling a diode in series with the signal connection to the second layer 62. In addition, more than one diode may be used depending upon the magnitude of the voltage generated across a layer. The system switches from transmit to receive mode immediately after completion of a transmit pulse.

Figure 7:
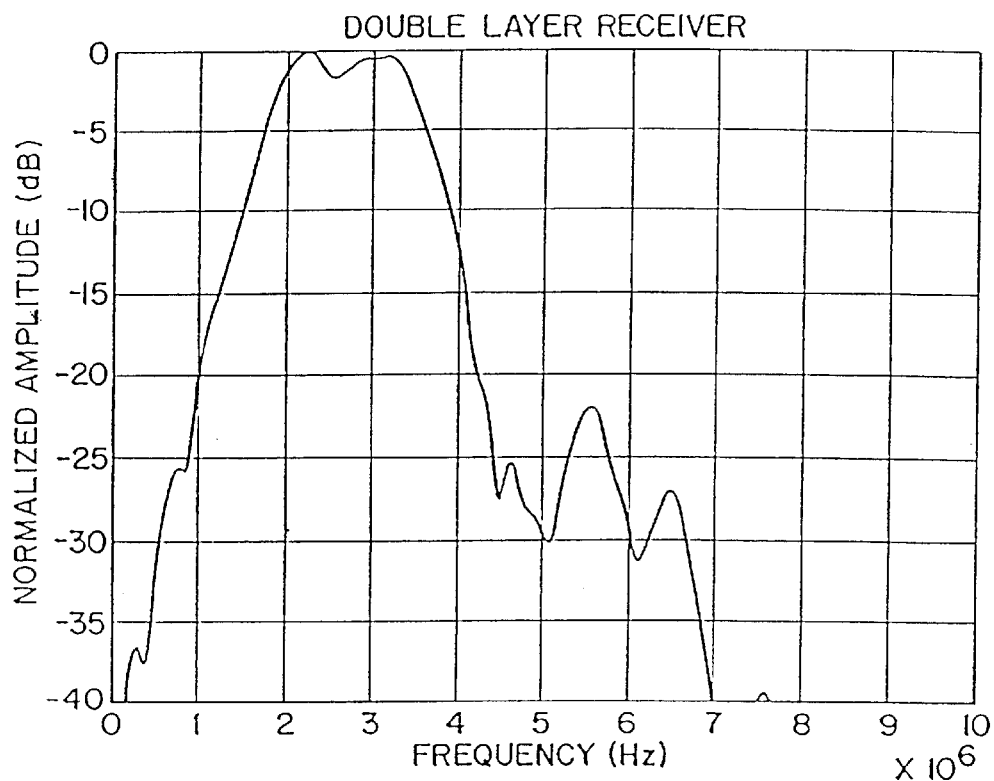
FIG. 7 is a graph illustrating the receive response of a double layer transducer in which both layers are connected in parallel.

FIG. 7 is a graph illustrating the receive response of a double layer transducer in which both layers are electrically connected in parallel as they are in transmission. In this embodiment each piezoelectric layer was about 0.25 mm thick, about 14 mm long and about 0.265 mm wide. A high impedance acoustic matching layer having a thickness of about 0.126 mm and a low impedance matching layer having a thickness of 0.087 mm were used. The center frequency of the excitation signal was about 2.8 MHz and at the second harmonic, 5.6 MHz, the response was considerably attenuated as shown.

Figure 8:
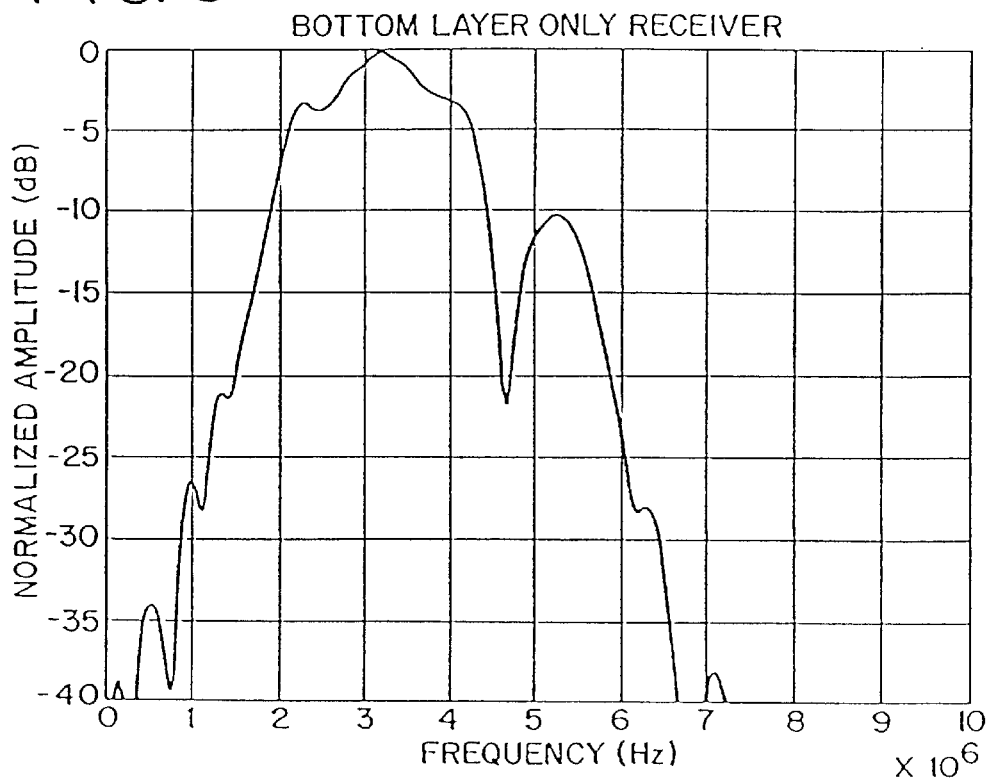
FIG. 8 is a graph illustrating the receive response of the same transducer of FIG. 7 with only the bottom layer connected.

FIG. 8 is a graph illustrating the receive response of the same transducer as that used for FIG. 7 with only the bottom layer coupled to the transceiver during reception while the top layer is isolated. It can be seen from the graph that a significant increase in sensitivity in the vicinity of the second harmonic is produced.

Figure 9:
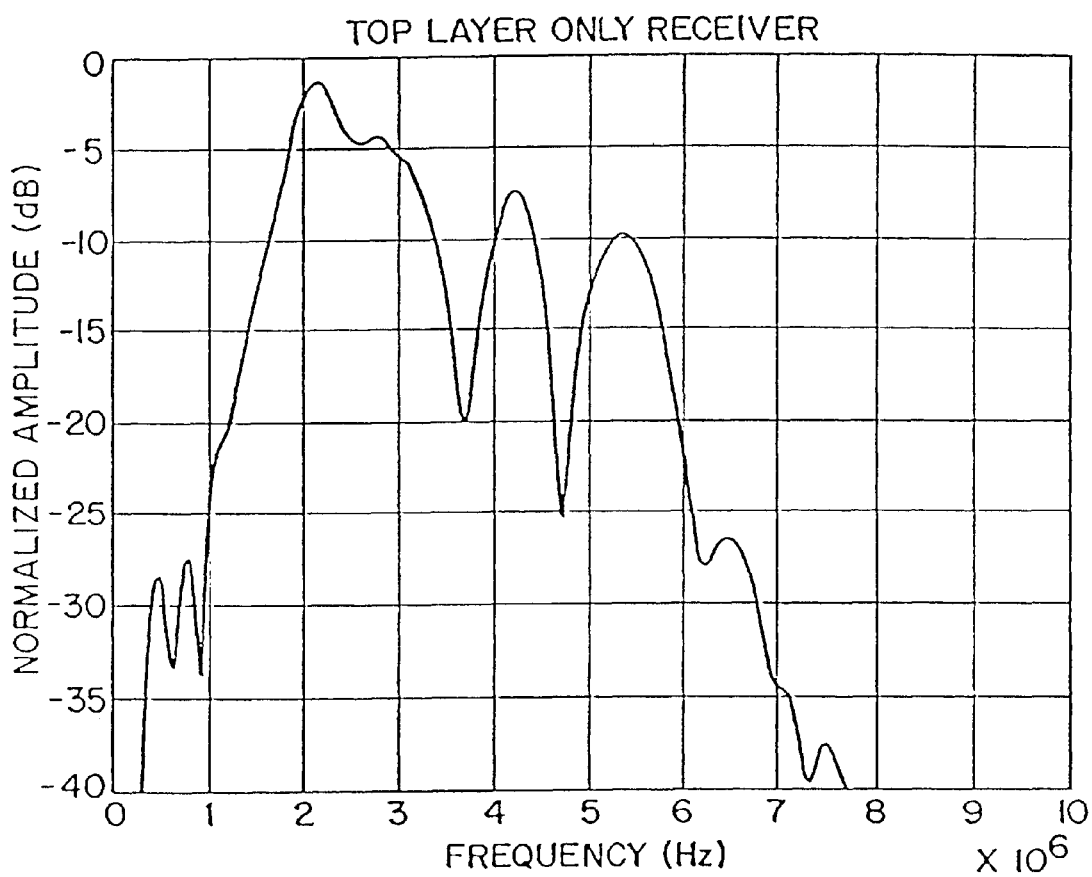
FIG. 9 is a graph illustrating the receive response of the same transducer of FIG. 7 with only the top layer connected.

FIG. 9 is a graph illustrating the receive response of the same transducer as that used for FIG. 7 with only the top layer coupled to the transceiver during reception while the bottom layer is isolated. Again, it can be seen that a significant improvement in sensitivity in the region of the second harmonic has occurred.

Experimentation can be used to optimize the performance of the transducer array varying the dimensions and materials employed.

Of course there are many alternative ways of isolating one or multiple layers of a multi-layer transducer during reception. FIGS. 10–15 illustrate several different preferred embodiments.

Figure 10:
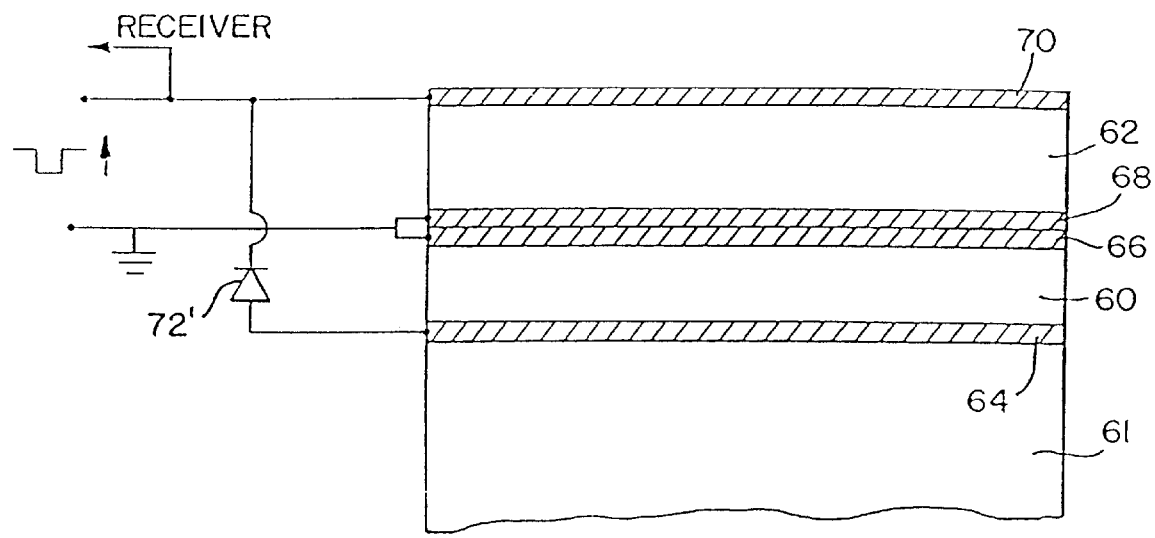
FIG. 10 illustrates a cross-sectional view taken along the elevation direction of a transducer array according to another preferred embodiment of the present invention.

FIG. 10 illustrates a cross-sectional view taken along the elevation direction of a transducer array according to another preferred embodiment of the present invention. The transducer shown in FIG. 10 is similar to that shown in FIG. 6 except that the excitation signal is now a negative pulse and therefore diode 72' is oriented in the opposite sense from that shown in FIG. 6. Otherwise the operation of the transducer is the same and need not be described again.

Figure 11:
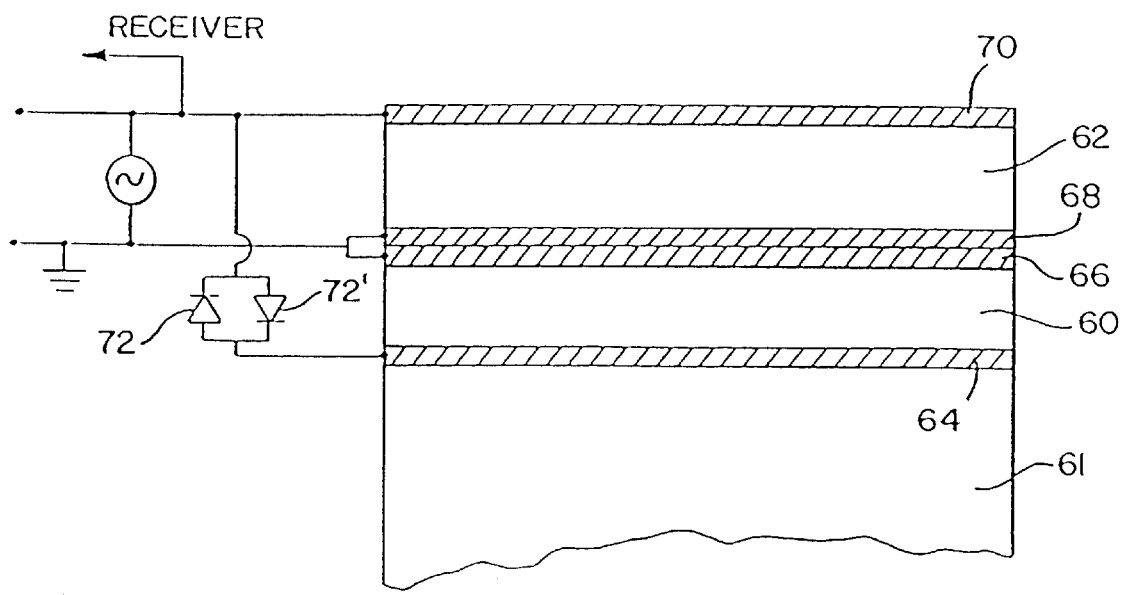
FIG. 11 illustrates a cross-sectional view taken along the elevation direction of a transducer array according to another preferred embodiment of the present invention.

FIG. 11 illustrates a cross-sectional view taken along the elevation direction of a transducer array according to another preferred embodiment of the present invention. In this embodiment the excitation signal is bipolar. Therefore, two diodes 72 and 72' coupled in parallel but in opposite orientations, are coupled in series with the first electrode 64 of the first layer 60 and the transceiver. Again, the diodes 72 and 72' allow the first layer 60 to be active during transmission while isolating the first layer 60 from the transceiver in the receive mode.

Figure 12:
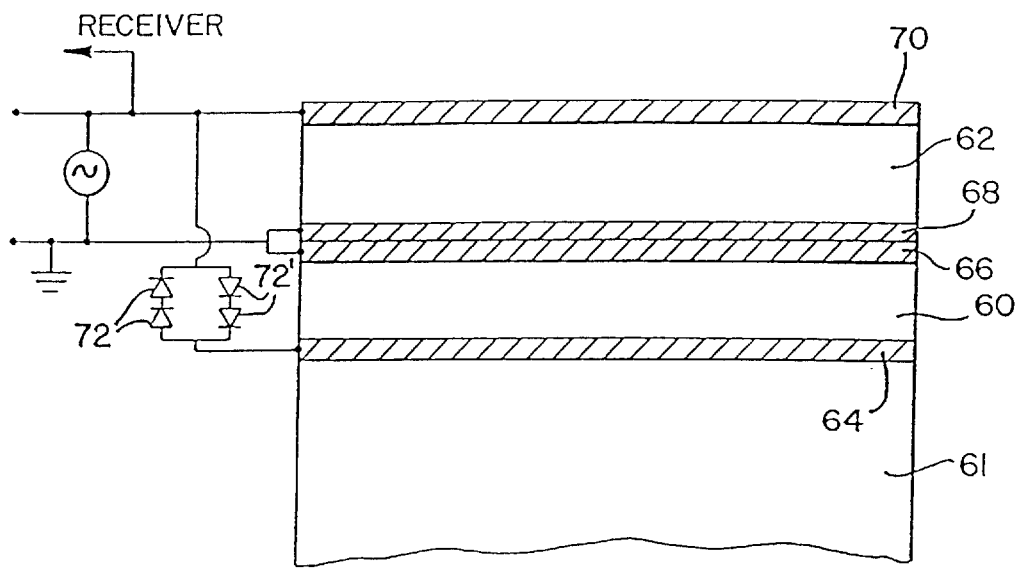
FIG. 12 illustrates a cross-sectional view taken along the elevation direction of a transducer array according to another preferred embodiment of the present invention.
Figure 15:
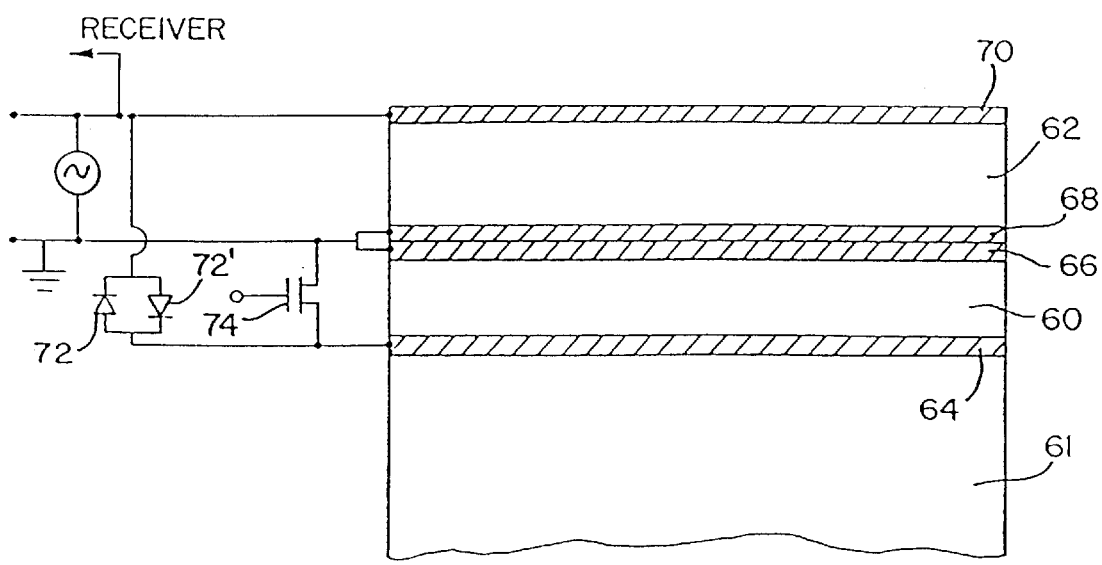
FIG. 15 illustrates a cross-sectional view taken along the elevation direction of a transducer array according to another preferred embodiment of the present invention.

FIG. 12 illustrates a cross-sectional view taken along the elevation direction of a transducer array according to a preferred embodiment of the present invention. The transducer shown in FIG. 15 is similar to that shown in FIG. 11 except that multiple diodes are used in each branch of the arrangement. Providing additional diodes ensures isolation between the first layer 60 and the transceiver should voltages larger than the diode turn-on voltage of one diode be developed across the first layer 60.

Figure 13:
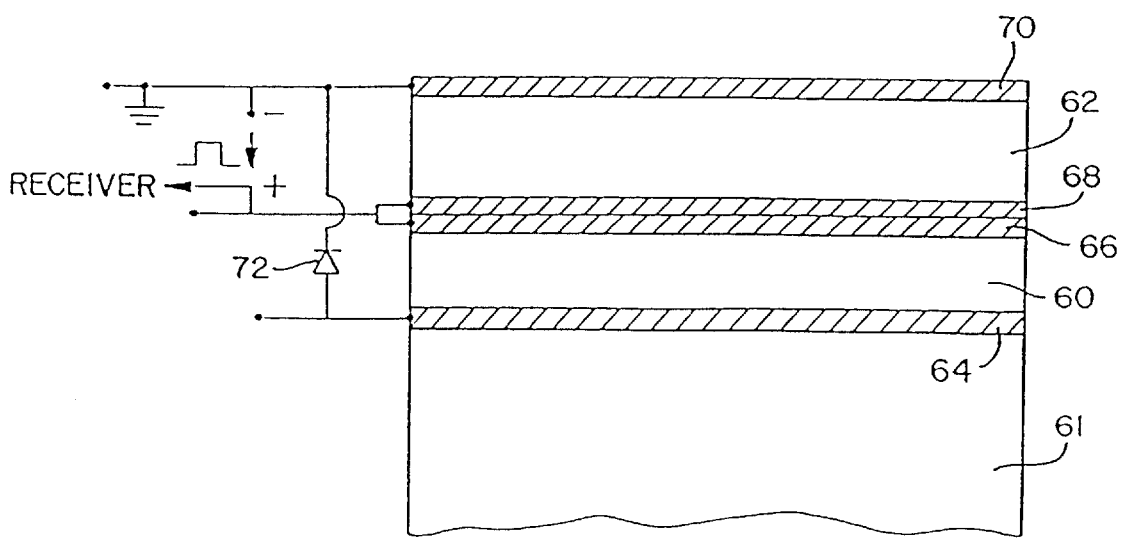
FIG. 13 illustrates a cross-sectional view taken along the elevation direction of a transducer array according to another preferred embodiment of the present invention.

FIG. 13 illustrates a cross-sectional view taken along the elevation direction of a transducer array according to a preferred embodiment of the present invention. In this embodiment the first electrode 64 of the first layer 60 is coupled to ground through diode 72. The second electrode 70 of the second layer 62 is coupled directly to ground. The second electrode 66 of the first layer 60 and the first electrode 68 of the second layer 62 are coupled to the transceiver. This configuration has the advantage that a ground potential electrode is placed closer to the patient and hence a safety improvement is obtained.

Figure 14:
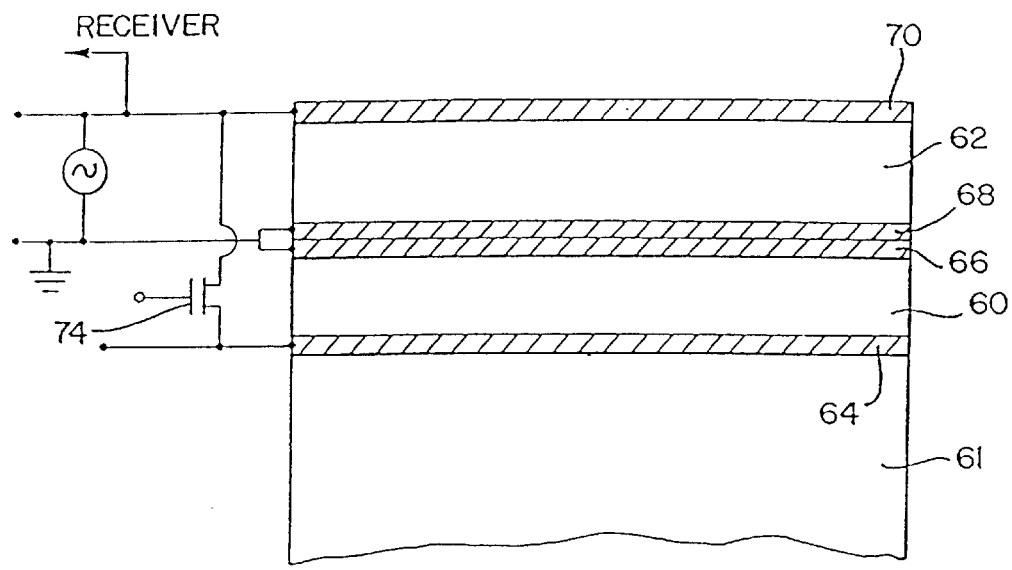
FIG. 14 illustrates a cross-sectional view taken along the elevation direction of a transducer array according to another preferred embodiment of the present invention.

FIG. 14 illustrates a cross-sectional view taken along the elevation direction of a transducer array according to a preferred embodiment of the present invention. The array shown in FIG. 14 is similar to that shown in FIG. 11 except that the diode has been replaced by a transistor 74. The transistor 74 is controlled by an externally applied bias signal which is supplied during transmit to turn on the transistor 74. This effectively connects the hot wire supply to electrode 70 to the wire leading to electrode 64 resulting in dual layer operation in transmit. During receive, the transistor 74 is switched off isolating the received voltage generated from layer 60 from that generated across layer 62.

FIG. 15 illustrates a cross-sectional view taken along the elevation direction of a transducer array according to a preferred embodiment of the present invention. In this arrangement, a bipolar excitation signal may be applied to both layers in transmit. In the reception mode, one layer is short circuited by transistor 74. This eliminates the contribution of the second layer to the net received signal. Creating a short circuit across the second layer may have the advantage of reducing cross-talk noise from the second layer interfering with the first layer or adjacent layers in proximal transducer elements. In order to prevent short circuiting the desired signal layer back to back diodes 72 and 72' are provided to isolate the short circuited layer in the event that the receive voltages do not exceed the diode turn-on voltage. Generally the receive signal will not exceed this voltage.

Various modifications may be made to the preferred embodiments illustrated. As shown, the diodes used to isolate the first layer may be replaced by a transistor controlled by an externally applied bias signal. One bias signal can be used for the entire array. Alternatively, the diode can be replaced by an electromechanical switch such as a relay. Of course other means of isolation may be used. For example, any semiconductor device whose electrical conductance may be controlled either by external bias signal or by the transmit pulse itself.

In addition, the ultrasound transducer array may be operated so that it switches between receiving on both layers for optimal conventional imaging and only on one layer for optimal contrast agent detection. More particularly, a single layer would be used in receive for a predetermined time interval after a transmission pulse. This is determined by the maximum useful range of single layer receiver system. The second layer would be switched back on to bring back optimal imaging sensitivity at the fundamental frequency. A predetermined weighting factor would be applied to the line data at the same time to suppress a dramatic change in brightness at the range corresponding to the switching time. Second harmonic data at ranges greater than the range/time of switch on would be largely lost but presumably the field of interest for second harmonic energy would be in the nearer portion of the field of view and hence would not present a problem. The two scans could be interleaved and presented on a display screen together. Such an application could be performed using the embodiments shown in FIGS. 14 and 15 where the bias voltage would be applied to the transistor according to whether or not the response of the first layer was to be isolated.

Also, while only two layers have been illustrated, more than two layers can be used. During the receive cycle switching between single and multiple layer operation may be desired.

In addition, the first and second layers do not have to be of uniform thickness. For example, both layers may have the variable thickness disclosed in U.S. Pat. Nos. 5,415,175 and 5,438,998 which are specifically incorporated herein by reference. Also, the present invention may be implemented with a curved ceramic and a low loss polyurethane filler instead of a lens.

The diode or diodes used to isolate a layer or layers should be selected based on their ability to withstand the design voltages and currents. Motorola MMAD 1108, a 16 pin surface mount package, with eight separate diodes, may be suitable for use in a transducer since package size is an issue. If a transistor is used for isolation, preferably a MOSFET such as National Semiconductor's IRF530 may be used. The selection of the transistor should be based on its ability to withstand the expected voltages and currents and preferably has a low "on" resistance and input capacitance.

The transducer described above may also include one or more filters that are responsive to the switching devices (e.g. diodes or transistors). One or more tuning elements, such as inductors, capacitors and resistors, are connected in series and/or parallel with the switching devices. The tuning elements affect the spectral response of the transducer. For example, an inductor connected in series with a transducer element and/or cable balances the capacitance of the element and/or cable. These tuning elements may also provide high, low or band pass filtering.

By connecting the tuning elements in series or parallel with the switching devices, the transmit or receive signals are switchably filtered. For example, energy at harmonic frequencies is low or band pass filtered from transmit signals or energy at fundamental frequencies is high or band pass filtered from receive signals. The filters are isolated by the switching devices so that the fundamental signal is transmitted and the harmonic signal is received. Filtering smoothes the spectral response and reduces noise by reducing the impact of out of band thermal noise. Thermal noise is related to the square root of frequency bandwidth and may be preferentially reduced by setting band, low or high pass limits to pass desired signal components and reduce out of band noise.

Figure 16A:
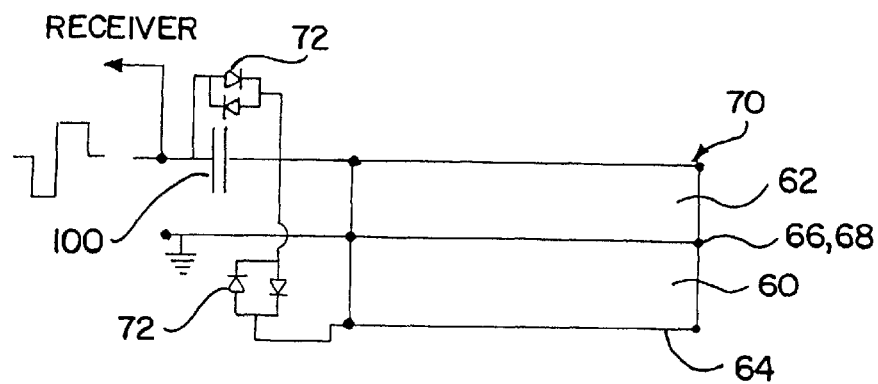
FIGS. 16A–C are circuit diagrams illustrating a cross-sectional view taken along the elevation direction of a transducer array according to other preferred embodiments of the present invention.
Figure 16B:
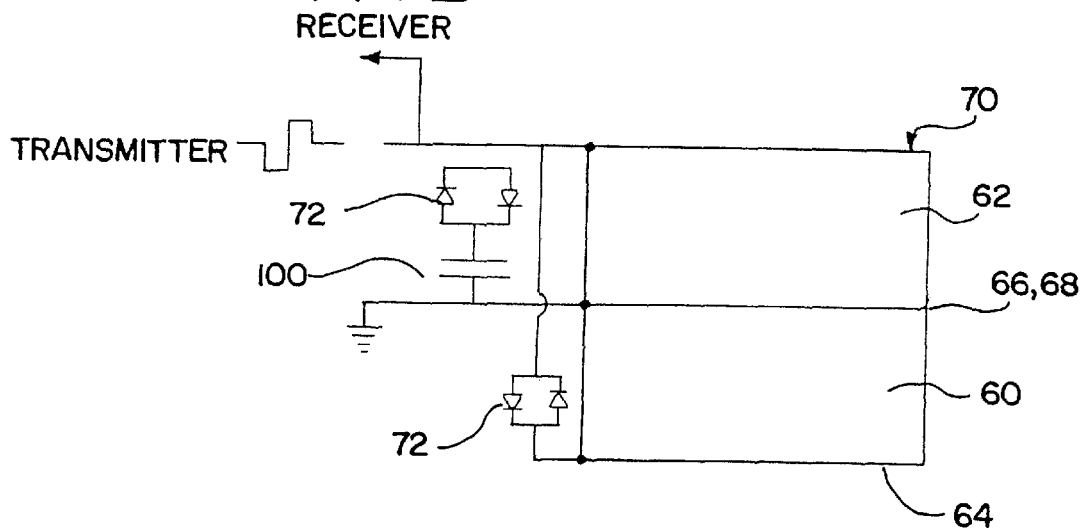
Figure 16C:
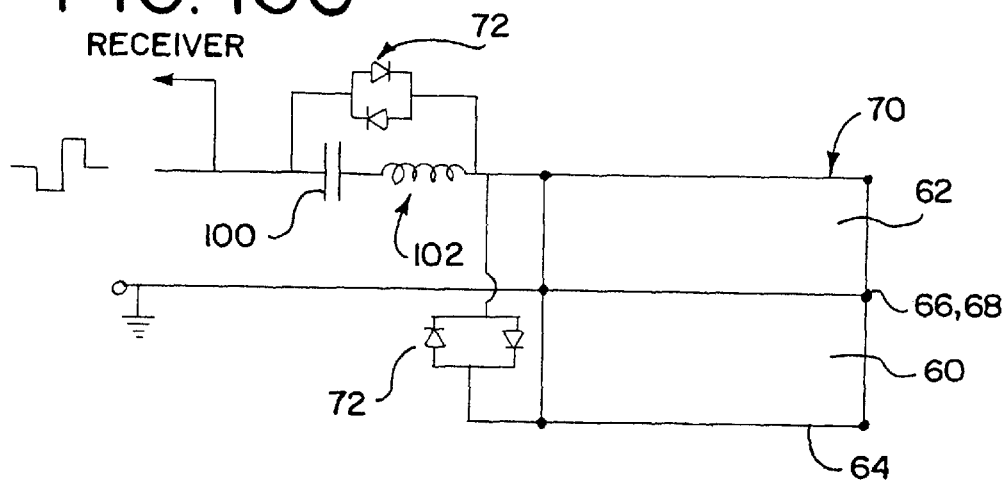

FIGS. 16A–C show high, low and band pass filter circuits, respectively. FIG. 16A illustrates a cross-sectional view taken along the elevation direction of a transducer array. Two diode pairs 72 switchably couple electrodes 64 and 70. The electrode or electrodes 66, 68 between the two layers 60 and 62 is coupled to ground. A capacitor 100 is coupled in parallel with the diode pairs 72 and in series with a resistance of approximately 50 ohms provided by the receiver. A resistor separate from the receiver or other values of resistance may be used. Additional tuning elements may be used.

The capacitor 100 and receiver resistance operate as a high pass filter. The diode pairs 72 switch in the filtering components during transmit operation and allow high pass filtering of receive signals during receive operation. The value of the capacitor 100 and other tuning components are preferably selected to provide a high pass cut-off frequency between the fundamental and harmonic bands of interest. During the receive operation, the diodes operate as open circuit and isolate capacitor 100.

FIG. 16B illustrates a cross-sectional view taken along the elevation direction of a transducer array. One diode pair 72 switchably couples two electrodes 64 and 70. Another diode pair 72 switchably couples the center electrode or electrodes 66, 68 with one of the outer electrodes 70. The center electrode or electrodes 66, 68 between the two layers 60 and 62 is coupled to ground. The capacitor 100 is coupled in series with one of diode pairs 72 between ground and the transceiver and in series with a source impedance of the transmitter. Additional tuning elements may be used.

The capacitor 100 and transmitter impedance operate as a low pass filter. The diode pairs 72 switch in the filtering components during receive operation and allow low pass filtering of transmit signals during transmit operation. The value of the capacitor 100 and other tuning components are preferably selected to provide a low pass cut-off frequency between the fundamental and harmonic bands of interest. During the receive operation, the diodes operate as an open circuit and isolate the capacitor 100.

FIG. 16C illustrates a cross-sectional view taken along the elevation direction of a transducer array. One diode pair 72 switchably couples two electrodes 64 and 70. Another diode pair 72 switchably couples in parallel with the capacitor 100 and an inductor 102. The center electrode or electrodes 66, 68 between the two layers 60 and 62 is coupled to ground. The capacitor 100 is coupled in series with one of diode pairs 72 and in series with a resistance of the receiver. Additional tuning elements may be used.

The capacitor 100, inductor 102 and receiver resistance operate as a band pass filter. The diode pairs 72 short circuit the filtering components during transmit operation and allow band pass filtering of received signals during receive operation. The value of the capacitor 100, the inductor 102 and other tuning components are preferably selected to provide a band pass cut-off frequency surrounding the harmonic band of interest. A series impedance minimum is produced at a resonant frequency, such as the harmonic frequency.

Other combinations of tuning components may be used, including one or more of capacitors, inductors and resistors in series and/or parallel arrangements. For example, filters with sharper cut-offs are used. Any of the different switching devices discussed above may be used. Filtering may be provided for both transmit and receive operation. As another example, a transistor is used as the switching device and the same control signal is used to select one or more tuning components or otherwise change a characteristic of the filter. As used herein, isolation includes switching out via an open circuit in a series connection and short circuiting via a short in a parallel connection.

The transducers described above may be used in both tissue and contrast agent harmonic imaging. In tissue harmonic imaging, no additional non-linear contrast agent is added to the target or area under examination, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In this case no additional non-linear contrast agent is introduced into the tissue at any time during the imaging session.

For contrast agent harmonic imaging, any one of a number of well known contrast agents, such as microspheres containing a gas, may be added to the target in order to provide a harmonic response. For this reason, it should be understood that the introduction of an added contrast agent into the tissue being imaged is not implied in any of the following claims unless such added non-linear contrast agent is expressly recited.

It is to be understood that the forms of the invention described herewith are to be taken as preferred examples and that various changes in the shape, size and arrangement of parts may be resorted to, without departing from the spirit of the invention or scope of the claims.

What is claimed is:

1. An ultrasound transducer probe for transmitting an ultrasound beam into an area of examination and receiving signals reflected from said area of examination, the ultrasound transducer probe comprising:

a first layer having a first electrode on one side of said first layer and a second electrode on an opposite side of said first layer wherein said first layer emits an ultrasound beam when a transmit signal is applied to said first and second electrodes and said first layer develops a receive signal across said first and second electrodes upon receipt of an ultrasound beam reflected back from said area of examination;

a second layer disposed on said first layer, said second layer having a third electrode on one side of said second layer and a fourth electrode on an opposite side of said second layer wherein said second layer emits an ultrasound beam when a transmit signal is applied to said third and fourth electrodes and said second layer develops a receive signal across said third and fourth electrodes upon receipt of an ultrasound beam reflected back from said area of examination;

means for isolating said receive signal developed across said second layer; and at least one tuning component selected from the group consisting of: an inductor, a capacitor, a resistor and combinations thereof connected with the means for isolating.

2. An ultrasound transducer according to claim 1 wherein said second electrode and said third electrode comprise one electrode.

3. The ultrasound transducer of claim 1 wherein the at least one tuning component is connected with one of the first, second and third electrodes.

4. The ultrasound transducer of claim 1 wherein the at least one tuning component is connected in parallel with the means for isolating.

5. The ultrasound transducer of claim 1 wherein the at least one tuning component is connected in series with the means for isolating.

6. The ultrasound transducer of claim 1 wherein the at least one tuning component comprises an inductor connected in series with the means for isolating.

7. The ultrasound transducer of claim 1 wherein the at least one tuning component comprises a filter.

8. The ultrasound transducer of claim 7 wherein the filter comprises a high pass filter.

9. The ultrasound transducer of claim 7 wherein the filter comprises a band pass filter.

10. The ultrasound transducer of claim 7 wherein the filter comprises a low pass filter.

11. The ultrasound transducer of claim 8 wherein the means for isolating is operable to allow high pass filtering of the receive signal.

12. The ultrasound transducer of claim 10 wherein the means for isolating is operable to allow low pass filtering of the transmit signal.

13. The ultrasound transducer of claim 1 wherein said means for isolating comprises a diode.

14. The ultrasound transducer of claim 1 wherein said means for isolating comprises a transistor controlled by an externally applied bias voltage.

15. A method for imaging an area of examination by transmitting an ultrasound beam into said area of examination and receiving signals reflected back from said area of examination, the method comprising:

a) providing an ultrasound transducer having at least first layer and second layers, said second layer disposed on said first layer;

b) transmitting an ultrasound beam;

c) applying a signal across both said first and second layers during (b);

d) receiving signals generated across said first layer while e) isolating signals generated across said second layer during d); and f) filtering as a function of the isolation one of (i) transmit signals associated with c) and (ii) the received signals associated with d).

16. The method of claim 15 wherein f) comprises connecting at least one tuning component selected from the group consisting of: a inductor, a capacitor, a resistor and combinations thereof with a means for isolating signals generated across said second layer.

17. The method of claim 15 further comprising:

g) switching from receiving signals generated across said first layer while isolating signals generated across said second layer and receiving signals generated across both said first and second layers;

wherein f) comprises filtering while isolating signals generated across said second layer without filtering while receiving signals generated across both said first and second layers.

18. The method of claim 15 further comprising:

g) switching from receiving signals generated across said first layer while isolating signals generated across said second layer and receiving signals generated across both said first and second layers;

wherein f) comprises filtering the received signals generated across both said first and second layers without filtering while isolating signals generated across said second layer.

19. The method of claim 15 wherein f) comprises high pass filtering.

20. The method of claim 15 wherein f) comprises band pass filtering.

21. The method of claim 15 wherein f) comprises low pass filtering.

22. The method of claim 19 wherein f) comprises high pass filtering of the receive signal without filtering a transmit signal as a function of the isolation.

23. The method of claim 15 wherein f) comprises low pass filtering of the transmit signal without filtering the receive signal as a function of the isolation.

24. The method of claim 15 wherein b) comprises transmitting the ultrasound beam into said area of examination, said area of examination being substantially free of contrast agent throughout an entire imaging session.

25. An ultrasound transducer comprising:

a first transducer layer physically coupled to a transceiver;

a second transducer layer physically coupled to the transceiver;

means for electrically coupling the first and second layers to the transceiver during a transmit mode and electrically decoupling one of the first and second layers from the transceiver during a receive mode; and a filter operative to filter during one of the transmit mode and the receive mode as a function of the electrical coupling without filtering during the other of the transmit and receive modes.

26. The ultrasound transducer of claim 25 wherein the means for electrically coupling and decoupling comprises a transistor coupled between the second layer and the transceiver.

27. The ultrasound transducer of claim 25 wherein the means for electrically coupling and decoupling comprises at least one diode coupled between the second layer and the transceiver.

28. The ultrasound transducer of claim 25 wherein the filter is connected in series with the means for electrically coupling and decoupling.

29. The ultrasound transducer of claim 25 wherein the filter is connected in parallel with the means for electrically coupling and decoupling.

30. The ultrasound transducer of claim 25 wherein the filter filters out fundamental frequencies where the second layer is decoupled from the transceiver.

31. The ultrasound transducer of claim 25 wherein the filter filters out harmonic frequencies where the second layer is coupled to the transceiver.

32. The ultrasound transducer of claim 25 wherein the filter comprises a tuning element selected from the group consisting of: an inductor, a capacitor, a resistor and combinations thereof.

33. A method for imaging an area of examination by transmitting an ultrasound beam into said area of examination and receiving signals reflected back from said area of examination, the method comprising:
   a) providing an ultrasound transducer having at least first layer and second layers, said second layer disposed on said first layer;
   b) transmitting an ultrasound beam into said area of examination, said area of examination being substantially free of contrast agents during an entire imaging session;
   c) applying a signal across both said first and second layers in (b);
   d) receiving signals generated across said first layer; and
   e) isolating signals generated across said second layer during d).

34. The method of claim 33 further comprising:
   f) filtering as a function of the isolation one of (i) transmit signals associated with c) and (ii) the received signals associated with d).

35. The method of claim 34 wherein f) comprises connecting at least one tuning component selected from the group consisting of: a inductor, a capacitor, a resistor and combinations thereof with a means for isolating signals generated across said second layer.

36. The method of claim 34 wherein f) comprises high pass filtering.

37. The method of claim 34 wherein f) comprises band pass filtering.

38. The method of claim 34 wherein f) comprises low pass filtering.

39. The method of claim 36 wherein f) comprises high pass filtering of the receive signal without filtering a transmit signal as a function of the isolation.

40. The method of claim 38 wherein f) comprises low pass filtering of the transmit signal without filtering the receive signal as a function of the isolation.

41. The method of claim 33 wherein e) comprises switching with a diode.

42. The method of claim 33 wherein e) comprises switching with a transistor.

* * * * *